United States Patent [19]
Barnett et al.

[11] 4,087,555
[45] May 2, 1978

[54] SKIN CREAM CONTAINING MILK PROTEIN

[75] Inventors: Gabriel Barnett, New York; Nathan Gershaw, Commack; Jack J. Mausner, East Hills, all of N.Y.

[73] Assignee: Helena Rubinstein, Inc., New York, N.Y.

[21] Appl. No.: 611,435

[22] Filed: Sep. 8, 1975

[51] Int. Cl.$^2$ .............................................. A61K 7/48
[52] U.S. Cl. .................................... 424/357; 252/316; 424/359; 424/360; 424/361; 424/362; 424/363; 424/365
[58] Field of Search ............... 424/357, 359, 361, 365, 424/360; 252/316

[56] References Cited
U.S. PATENT DOCUMENTS 3,340,153  9/1967  Kast ...................................... 424/359

*Primary Examiner*—Dale R. Ore
*Attorney, Agent, or Firm*—Burgess, Ryan and Wayne

[57] ABSTRACT

A skin cream composition having an oil phase, a water phase, and an encapsulated active base. The water phase includes hectorite clay and a peptizer for the clay. The encapsulated active base includes hectorite clay, a peptizer for the clay, and a polar group affording compound.

5 Claims, No Drawings

SKIN CREAM CONTAINING MILK PROTEIN

This invention relates generally to cosmetic compositions, and more particularly, this invention relates to a visible action skin cream.

Various types of skin creams are known in the art, these prior art compositions generally being oil-in-water emulsions containing a variety of active ingredients. The active ingredients could include, for instance, emollients, bactericides, moisturizers, and the like. The prior art compositions also contain, of course, an emulsifying agent and various other ingredients such as perfumes, coloring agents, and the like. Stabilizers were included to prevent separation of the two phases. Certain of the prior art compositions suffered from the disadvantage that there was still separation of the phases and others that were efficiently emulsified had the disadvantage of separation of the active ingredients even though the oil and water phases remained emulsified. Also, since the oil component of these compositions was literally an oil, these compositions when applied to the skin presented an oily appearance and were difficult to remove by ordinary washing.

It is therefore, an object of the present invention to provide a visible action skin cream which is free of the aforementioned and other such disadvantages.

It is another object of the present invention to provide a visible action skin cream which is easy and inexpensive to manufacture.

It is yet another object of the present invention to provide a visible action skin cream wherein the active ingredients are encapsulated and contained in an oil-in-water emulsion.

These and other objects of the present invention will become apparent from a consideration of the following description of the invention.

SUMMARY OF THE INVENTION

Consistent with the foregoing objects, the present invention is drawn to a composition for use as a skin cream comprising an oil phase, a water phase and an encapsulated active base. The oil phase comprises an emulsifier, an emollient, a lubricant, a dispersing agent, and a non-ionic surfactant. The water phase comprises hectorite clay, a peptizer for the clay, a humectant, milk protein, and water. The encapsulated active base comprises hectorite clay, a polar group affording compound, a peptizer for the clay, and water.

DESCRIPTION OF THE PREFERRED EMBODIMENT

Hectorite clay

The hectorite clays used in this invention are made up of silicon (Si), magnesium (Mg), lithium (Li), oxygen, hydroxyl (OH), may or may not contain fluorine (F), and an exchangeable cation. Exchangeable cations which have been observed are barium, calcium, cesium, hydrogen, lithium, magnesium, potassium, rubidium, sodium and strontium. Sodium and lithium are commonly present as this cation or cations, as two or more may be present.

Van Olphen gives the following general formula for half a unit cell of hectorite clay:

where M is an exchangeable cation. Fluorine (F) may or may not be present. Some hydroxyl is normally present.

Synthetic hectorite clays are available. Because of uniformity in quality and analysis, the synthetic hectorite clays are preferred over the clay derived from natural hectorite clay mineral. Some suppliers of synthetic hectorite clay are, LaPorte Industries under the trademark LAPONITE and Baroid Division National Lead Company under the trademark BARASYM. Synthetic hectorite clays can be made by the process disclosed in U.S. Pat. No. 3,586,478, granted to Barbara S. Neumann on June 22, 1971, and which is embodied herein by reference.

The Encyclopedia of Chemical Technology, 2nd Edition, Vol. 5, page 547, gives the following typical formula for hectorite clay, from a natural source:

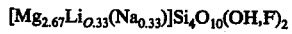

In Table 1, below, there is given the analysis of seven different hectorite clays. No. I is a natural clay and the analysis is taken from Ency. Chem. Tech., 2nd. Ed., Vol. 5, page 548. No. II is a beneficiated "90%" content natural hectorite supplied by Baroid under the trademark MACALOID. No's III, IV, and V are synthetic clays supplied by Baroid under the trademark BARASYM. No's VI and VII are synthetic clays supplied by LaPorte under the trademark LAPONITE.

TABLE I

| Analysis in Wt.% | Hectorite Clays | | | | | | |
|---|---|---|---|---|---|---|---|
| | I | II | III | IV | V | VI | VII |
| $SiO_2$ | 55.9 | 51.9 | 56.2 | 56.1 | 56.1 | 55.9 | 60.4 |
| MgO | 25.0 | 22.1 | 29.2 | 28.4 | 28.4 | 26.7 | 26.0 |
| $Li_2O$ | 1.1 | 1.2 | 2.3 | 2.1 | 0.5 | 1.9 | 1.1 |
| $Na_2O$ | 2.7 | 3.1 | 0.6 | 2.4 | 3.5 | 4.3 | 3.0 |
| F | 6.0 | 2.1 | 1.8 | 1.6 | 1.6 | 8.3 | 0.0 |
| CaO | 0.0 | 6.5 | 0.5 | 0.4 | 0.3 | 0.1 | 0.2 |
| $Fe_2O_3$ | 0.0 | 0.3 | 0.0 | 0.0 | 0.0 | 0.0 | 0.0 |
| $Al_2O_3$ | 0.1 | 0.8 | 0.0 | 0.0 | 0.0 | 0.0 | 0.0 |
| Ignition Loss | 12.1 | 11.7 | 11.4 | 9.5 | 9.5 | 3.6 | 6.9 |

Peptizer

It is preferred to work first with a thin (low viscosity) watery fluid composition of clay and water. This is accomplished by having present during the formation of the thin, watery fluid composition an amount of peptizer sufficient to prevent the formation of a gel, or adding sufficient peptizer to an already existing gel to destroy the gel. The thin, watery fluid composition facilitates blending of other components and the filling of the small containers often used in the cosmetics industry; also air bubbles and foaming can be more readily eliminated from the product composition before the filling of, and during the filling of, the containers. The final desired gel condition is produced by heating the fluid aqueous colloidal solution of hectorite clay and peptizer agent (and other components) to a temperature at which the fluid solution changes to a gel.

Any of the known peptizers may be used, such as, ammonia, hydrogen peroxide, sodium carbonate, sodium citrate, sodium hydroxide, sodium oxalate, sodium silicate, and water soluble salts of condensed phosphoric acids.

It is preferred to use as the peptizer one or more of the water soluble salts of a condensed phosphoric acid. (This nomenclature is taken from Ency. Chem. Tech., 2nd Ed., Vol. 15, pp. 241–257, John Wiley & Sons, 1968). The most preferred salts are water soluble ammonium, potassium, or sodium salts of the condensed phosphoric acid. Illustrative salts are: tetraammonium pyrophosphate; tetrapotassium pyrophosphate; tetrasodium pyrophosphate; ammonium tripolyphosphate; potassium tripolyphosphate; sodium tripolyphosphate; ammonium trimetaphosphate; potassium trimetaphosphate; sodium trimetaphosphate; ammonium tetrametaphosphate; potassium tetrametaphosphate; sodium tetrametaphosphate; and the phosphate glasses, such as, ammonium hexametaphosphate; potassium hexametaphosphate and sodium hexametaphosphate. (Water soluble is intended to mean herein "soluble enough to do the peptizing task".) Tetrasodium pyrophosphate and sodium hexametaphosphate are commonly used peptizers.

The amount of peptizer present will vary with the specific agent, the specific clay, the amount of clay present, and in some cases the other components present. When using one of the salts of a condensed phosphoric acid, in general, a peptizing amount is in the range of about 0.2–1 percent by weight.

The Gels

1. Gels without Peptizer Agent

Hectorite clays and water upon vigorous stirring form an aqueous colloidal solution; if enough clay is present a gel is formed.

The gel composition may include a foaming agent, such as, synthetic detergents, e.g., sodium lauryl sulfate, sodium N-lauroyl sarcosinate, and sodium lauryl sulfoacetate, and soaps, such as sodium stearate.

The gel composition may include essences coloring agents, either dissolved or in suspension; or oils such as those used in cosmetics.

The amount of clay used is dependent on the specific clay, the amount of humectant, if any, and the amounts, if any, of other components present in the composition and the gel rigidity desired. A gelling amount of the hectorite clay is used and, in general, this amount is in the range of about 1–5 weight percent.

2. Gels from Peptized Solutions

It has been discovered that a thin, watery fluid composition consisting essentially of water, hectorite clay, and peptizer changed to a gel by heating the fluid solution to a gelling temperature. Time is needed for the change to take place and the time is temperature- and peptizer- dependent.

The change to the gel condition takes place even when the fluid solution includes humectant, foaming agents, or other components, or any combination of these. It is to be understood that the presence of other components may cause the composition to lose its thin, watery fluid condition; however, the other components will not cause the fluid solution-other component composition to gel.

The amount of peptizer used will vary with the specific agent, the specific clay and the amount of clay present, and even the other components present as these can effect the gelling capacity of the clay. When the specific peptizer is one or more of the water soluble ammonium, potassium or sodium salts of a condensed phosphoric acid, the amount of peptizer agent present is an amount of about 0.2–1.0 percent by weight of the composition. When using peptizer a temperature of about 70°–100° C is usually used to change from the fluid to the gel condition.

Capsules and Particles

The gel composition of this invention includes suspended therein particles and capsules having a size above colloidal dimensions. The particles or capsules may be made in situ by the hereinafter described procedure. In general, particles consist solely of a water insoluble reaction product, whereas capsules include a payload (core) surrounded by a membrane (shell or wall). It must be understood that both payload and membrane (or the particle) must be acceptable for use in cosmetics.

The payload may be any material, liquid, semisolid, or solid, which is useful in the specific gel composition such as essences, colorings, and the like. The payload containing capsules are especially useful when the payload is water insoluble and it is desired that the "carrier", as in a skin cream be an aqueous gel medium. It is evident that capsules are particularly useful when a mixture of materials is desired with the effect being aesthetic and/or practical by avoidance of intermingling.

The particles and capsules are prepared by the reaction of (1) aqueous colloidal solutions of hectorite clay, and (2) certain polar group affording materials.

1. Polar group affording organic materials

Not every polar group affording organic material is suitable for use. Only those polar group affording organic materials are suitable which react with hectorite clay, in aqueous colloidal solution, to form water insoluble particles. For example, the lower molecular aliphatic alcohols, especially those having high solubility in water, do not react to form water insoluble particles; indeed, these compounds appear to solubilize the clay. It has been observed that cellulose derivatives may or may not react to form water insoluble particles. It is thought that steric hindrance may be the reason for this failure.

It is thought that because the clay in aqueous solution forms a sort of network with reactive sites distributed thereon, the polar group affording polymers, or even macromolecules, may or may not be able to react to form water insoluble particles; reaction seems to be dependent on the spacing of the polymer polar groups, and also on steric hindrance. In some, the polar group spacing is to far out of line with reactive sites of the clay to permit enough reaction to form the water insoluble particles.

The operative polar group affording organic materials cannot be defined merely by naming classes of polar group affording organic materials; each class contains some members that do not react with the aqueous colloidal solution of inorganic silicate.

A simple screening procedure has been devised for determining whether or not a particular polar group affording organic material will react with the aqueous colloidal solution of clay to form water insoluble particles.

One definition is, the polar group affording organic material is characterized by (1) the ability to form water insoluble particles having a size above colloidal dimensions when added to an aqueous colloidal solution of synthetic hectorite clay and tetrasodium pyrophosphate peptizing agent, with commingling, and (2) having been selected from the group consisting of (i) simple organic compounds having at least one polar group and (ii) organic hydrophilic colloids.

Another definition, of equal scope that above, is in the form of "named classes of compounds". Here, the reactive polar group affording organic compounds are selected from the group consisting of (a) simple organic compounds having at least one polar group, desirably these are further characterized by insubstantial solubility in water at ordinary temperatures; (b) water soluble alkali metal carboxyalkylcellulose and water soluble alkali metal carboxyalkylhydroxyalkylcellulose; (c) water soluble polysaccharides; (d) water soluble proteins; (e) water soluble resins: poly(vinyl alcohol), poly(ethyleneimine), poly(acrylamide), polyvinylpyrrolidone, sulfonated polymers, carboxylic polymers, their esters and alkali metal salts, and maleic copolymer derivatives; and (f) water soluble cellulose ethers.

In general, the process of the invention will be carried out at ordinary temperatures of about 15°–43° C. Insubstantial solubility or immiscibility appears to aid in the formation of water insoluble particles when the polar compound is added to the aqueous colloidal solution of clay.

"Water soluble" when used herein as part of the name of a polar group affording organic material is intended to be understood as used in the hydrophilic colloid art, that is, those materials forming colloidal solutions or stable swollen dispersions in water. In the main these materials have solubilities up to about 5 weight percent; some dissolve to a greater extent.

Water soluble polysaccharides are included herein in the understanding of the hydrophilic colloid art. This grouping includes starch and its chemically modified forms, such as, carboxymethylstarch, hydroxyethylstarch, and hydroxypropylstarch; pectin; the plant gums, such as arabic, guar, tragacanth, larch, karaya, and locust bean; the marine polysaccharides, such as, agar, alginate and carrageenan; fully synthetic polysaccharides with properties similar to the natural gums are now available and are included herein.

Water soluble proteins are included herein as understood by the colloid art; gelatin and casein are the best known.

Poly(vinyl alcohol), poly(ethyleneimine), poly(acrylamide), and polyvinylpyrrolidone are well known hydrophilic colloids and are available in many molecular weights.

Carboxylic polymers, their esters and alkali metal salts are available for polyacrylic acid, polymethacrylic acid, polyethacrylic acid, and hydrolysis products of maleic polymers. Alkali metal salts are available as produced from polymers such as poly(acrylamide) and poly(acrylonitrile).

Maleic copolymer derivatives provide water soluble polar polymers such as half-amides and half-esters, available commercially.

Sulfonated polymers are available from the sulfonation of insoluble polymers or from polymerization of monomers having sulfonate groups.

The water soluble alkali metal carboxyalkylcellulose is exemplified by sodium carboxyethylcellulose and sodium carboxymethylcellulose (commonly referred to as CMC). The water soluble alkali metal carboxyalkylhydroxyalkylcellulose is exemplified by sodium carboxymethylhydroxyethylcellulose. Commonly "alkyl" in these cellulosics has 1–3 carbon atoms. (Because of the presence of the carboxy groups, these cellulosics are not considered to be cellulose ethers.)

Water soluble cellulose ethers as used herein are hydrophilic colloids of the type alkylcellulose and hydroxyalkylcellulose and hybrids of these two. Exemplary are methylcellulose, ethylcellulose, methylethylcellulose, hydroxyethylcellulose, ethylhydroxyethylcellulose, and methyhydroxypropylcellulose. Commonly "alkyl" in the cellulose ethers has 1–3 carbon atoms.

Also suitable are the simple organic compounds having at least one polar group, which react with the clay to form water insoluble particles. The simple organic compounds are distinguished from the macromolecules and polymers. Preferred polar groups are hydroxyl and carboxyl. Desirably, the simple organic compounds have insubstantial solubility in water at ordinary temperatures, that is, readily form a separate organic compound phase distinct from the aqueous phase.

However, some compounds having substantial solubility in water may be useful in situations where a non-polar water immiscible material is to become part of the water soluble particle, that is, a payload containing capsule. The polar compound must be preferentially soluble in the non-polar water immiscible material.

Illustrative groups of simple organic polar compounds are: the aliphatic alcohols, monohydric, dihydric and polyhydric; the lower aliphatic carboxylic acids and the fatty acids. The aliphatic and aromatic amines and amides, and the esters and salts of these compounds.

"Organic hydrophilic colloid" as used herein is intended to mean: any organic compound capable of forming stable suspensions in water of particles having colloidal dimensions — smaller than one micron — or capable of forming colloidal solutions.

2. The Clay

The clay for use in making the capsules and the water phase is hectorite, either natural or synthetic. Synthetic hectorite clay is preferred.

3. The Screening Procedure

The screening procedure uses a standard aqueous colloidal clay solution; this clay reacts rapidly at ordinary room temperatures with simple spatula stirring of the 'test' polar group affording organic material. Visual observation of the contents of the transparent bottle in which the procedure is performed is sufficient to show the formation of water insoluble particles of greater than colloidal size.

The standard solution is made up as follows: One part by weight of tetrasodium pyrophosphate peptizer agent is dissolved in ninety (90) parts by weight of water; then nine (9) parts by weight of Baroid synthetic fluorine (1.8%) hectorite clay (BARSYM LIH-200) are added to the peptized water; the peptized water and the clay are agitated for eight (8) hours with a Cowles blade at about 1,000 rpm to ensure the formation of a thin, watery fluid aqueous colloidal solution; forty (40) parts by weight of the aqueous colloidal solution are blended with sixty (60) parts by weight of water to form the standard solution which consists of, in weight percent, water, 96.0; clay, 3.6; and tetrasodium pyrophosphate, 0.4. The standard solution is translucent with a faint bleached-straw color.

The analysis of the standard clay is shown in Table 1, supra. It has: a base exchange capacity (meq/100 g) of 60–70; a color and appearance of a fine, white powder; screen analysis is −200 mesh; the bulk density is 60 lb/cu ft; and the pH of a 15 centipoise solution is 9.5. It has been observed that clay deviating somewhat from the foregoing analysis can be used successfully in the screening procedure.

In the screening procedure, 100 cc of the standard clay solution is placed in a transparent bottle, typically a screw cap bottle of about 300 cc volume. Then about 25 cc of the specific polar material being tested is added to the bottle. If the specific polar material is a liquid, it is added "as is". If it is a solid, it is dissolved in water and 25 cc, sometimes 50 cc as a check, is added to the bottle. Usually the commingling imparted by the pouring of the test material into the bottle is enough to produce water insoluble particles — if the test material is reactive. Otherwise a mild shaking of the contents is sufficient. In most cases direct visual observation sees the water insoluble particles, very small particles can be detected by viewing the wetted interior surface of the bottle by transmitted light. This indirect viewing overcomes the obstruction of a colored aqueous solution, or confirms the absence of particles.

Illustration I. Particles

Hydroxyethylcellulose (Cellosize QP4400, trademark of Union Carbide Corporation) was dissolved in water to give a two (2) weight percent solution; this solution was a transparent, water-white liquid. Fifty (50) cc of the 2% solution was poured in 100 cc of the standard clay solution and gently stirred with a spatula. Immediately the visual appearance of the contents changed to a turbid gray slurry. After turning the bottle sideways, gray strands were observed on the wetted interior surface. These strands were a gray-tan color, 2-3 mm wide and 6-15 mm long. The water insoluble strands drifted in the continuous aqueous phase and settled very slowly. During shelf over some time, there was no detectable merging (coalescence) of the strands; they retained their discrete nature.

Having discussed the broad aspects of the present invention, reference is had to the following Example of the preparation of the composition of the present invention. In the Example, certain ingredients are shown by trademark, the composition of these ingredients being as follows:

| | |
|---|---|
| Wickenol 155 | 2-ethylhexyl palmitate |
| Myrj 52 | polyoxyethylene stearate |
| Span 65 | sorbitan tristearate |
| Lactolysate | milk protein |
| | Supplier: Laboratoires Serobiologiques, Nancy, France |
| Cellosize WP 4400 | hydroxyethyl cellulose |
| DC Red 30 | 6,6'-dichloro-4-4'-dimethylthioindigo. |

EXAMPLE

Encapsulated Active Base

The encapsulated active base includes the following ingredients in percent by weight:

| | |
|---|---|
| Cellosize WP-4400 | 0.5 – 2.50 |
| Deionized water (A) | to make 100 |
| Clay-Rheo-VIS | 0.45 – 1.8 |
| Sodium acid pyrophosphate (Food Grade) | 0.05 – 2.00 |
| Deionized Water (B) | 4.5 –18.00 |
| DC Red 30 | 5 –10 |
| Casein Edible 80-mesh | 0.5 – 3.00 |
| Tegosept M (methyl paraben) | 0.4 |

The deionized water (A) was transferred to a stainless steel kettle equipped with a Lightnin' Mixer. The Lightnin' Mixer was started to run at a fairly rapid speed and the cellosize was sprinkled into the kettle. This was mixed until completely dissolved.

The deionized water (B) was transferred to a separate stainless steel container equipped with a Lightnin' Mixer. The mixer was started and the sodium acid pyrophosphate was added. The clay was sprinkled into the container and the mixture was stirred well to allow the clay to hydrate fully.

When the clay was hydrated, the clay-peptizer-water mixture was added to the Cellosize solution and mixed well. The DC Red was added and stirred in well and then the casein and Tegosept were added and stirred well. The entire mixture was put through a homogenizer or colloid mill.

Oil Phase

The oil phase contains the following ingredients, in parts by weight:

| | |
|---|---|
| Glyceryl Monostearate | 1.5 – 3.5 |
| Cetyl Alcohol | 1.25 – 2.5 |
| Wickenol 155 | 8.00 – 14.00 |
| Iso Stearic Acid 875 D | 0.5 – 4.00 |
| Myrj #52 | 0.2 – 1.50 |
| Span 65 | 0.1 – 0.4 |

Water Phase

The water phase includes the following ingredients, in percent by weight:

| | |
|---|---|
| Deionized Water | to 100 |
| Clay Rheo-VIS | 1.80 – 3.96 |
| Sodium Acid Pyrophosphate (Food Grade) | 0.20 – 0.44 |
| Propylene Glycol | 2.00 – 5.00 |
| Tegosept M (methyl paraben) | 0.40 |
| Triethanolamine | 1.00 |
| Lactolysate LS HR2 | 1.25 |
| Additionally, a perfume, Perfume 802 was included. | |

Mixing Procedure

The water of the water phase was tranferred to a kettle equipped with a Silverson Mixer and a sweep anchor Mixer. The Silverson Mixer was started and the sodium acid pyrophosphate was added and dispersed well. The clay was sprinkled in and stirred well until hydrated, approximately 10 minutes.

In a separate stainless steel container, the propylene glycol was weighed. The preservative and Tegosept were dissolved in the propylene glycol and then this solution was added to the kettle containing the clay and peptizer. The triethanolamine and the lactolysat were then added.

All the ingredients of the oil phase were transferred to a stainless steel steam-jacketed kettle. Both the oil and water phases were heated to 167° F (75° C) and the Silverson Mixer was continued in the water phase during the heating. When both phases reached 167° F, the oil phase was strained through a cloth into the water phase. The mixture was allowed to stir for ten minutes and then it was allowed to cool to 136° F (58° C). The perfume (0.20 part by weight) was added.

The Silverson Mixer was removed and replaced with an adequate Lightnin' Mixer. With the Lightnin' Mixer running at a moderately fast speed, but in a position which would not aerate the cream, 0.1 part by weight of the encapsulated active base was added. Stirring with the Lightnin' Mixer was continued until the particles broke up to the desired size. The composition was allowed to cool, with stirring, to 86° F (30° C) and then to room temperature. Stirring was stopped and the composition was tested.

The cream spread easily unto the skin and was not sticky or oily.

The skin cream composition of the present invention is used as a conventional day or night cream. By applying conventional quantities to the face, neck or forehead in a rotating manner, and massaging in the usual way, the encapsulated particles will break down easily and smoothly.

This product was tested on 100 women and shown to have significant improvements with respect to softness and smoothness of the skin after only 20 days of use. The product is, therefore, a very effective softener and a smoothing and moisturizing agent.

It has been found that certain practical limits of the critical ingredients can be set. For instance, the clay in the water phase of the emulsion should be present in an amount of up to about 3-5% by weight. The peptizer in the clay is used in an amount of about 0.2-1.0%. In the encapsulated active base, the limits are about 1 to 2 parts of clay to 2 to 3 parts cellulose. The preferred proportion is 2 parts clay to 3 parts cellulose on a dry basis.

It should be apparent from the foregoing detailed description that the objects set forth above have been successfully achieved. Moreover, while there is shown and described a present preferred embodiment of the invention it is to be distinctly understood that the invention is not limited thereto but may be otherwise variously embodied and practiced within the scope of the following claims.

Accordingly, what is claimed is:

1. A skin cream composition comprising an oil phase, a water phase, and an encapsulated active base;
   (A) said oil phase comprising, in parts by weight, 1.5-3.5 parts of an emulsifier, 1.25-2.5 parts of an emollient, 8.0-14.0 parts of a lubricant, 0.5-4.0 parts of a dispersing agent, and 0.3-2.0 parts of a non-ionic surfactant;
   (B) said water phase comprising, in parts by weight of up to about 5 parts of hectorite clay, 0.2-1.0 parts of a peptizer for said clay, up to 5.0 parts of a humectant, 1.2 parts of milk protein and the balance water; and
   (C) said encapsulated active base comprising, in parts by weight, 0.45-1.8 parts of hectorite clay, 0.05-2.0 parts of a polar group affording organic compound (1) characterized as being reactable with said hectorite clay to form water-insoluble particles having a size above colloidal dimensions when added to an aqueous colloidal solution of synthetic hectorite clay and tetrasodium pyrophosphate and (2) selected from the group consisting of a simple organic compound having at least one polar group characterized by insubstantial solubility in water at ordinary temperatures and (3) and organic hydrophilic colloid, 0.2-1 parts of a peptizer for said clay and the balance water.

2. A composition as claimed in claim 1, wherein:
   (A) said oil phase comprises glyceryl monostearate, cetyl alcohol, 2-ethylhexyl palmitate, isostearic acid, polyoxyethylene stearate, and sorbitan stearate;
   (B) said water phase comprises said hectorite clay, said peptizer, propylene glycol, triethanolamine, said milk protein, and said water; and
   (C) said encapsulated active base comprises said hectorite clay, hydroxyethyl cellulose, casein, said peptizer, and said water.

3. A composition as claimed in claim 2, wherein said hectorite clay is synthetic hectorite clay, said synthetic hectorite clay is present in said water phase in a gel-forming amount of up to about 5 percent by weight, said peptizer is sodium acid pyrophosphate and said sodium acid pyrophosphate is present in said water phase in an amount of about 0.2-1.0 percent by weight of said clay.

4. A composition as claimed in claim 2, wherein said clay is synthetic hectorite clay and the weight ratio of clay to hydroxyethyl cellulose is about 1-2:2-3.

5. A composition as claimed in claim 2, comprising:
   (A) an oil phase consisting essentially of, in parts by weight:

| | |
|---|---|
| glyceryl monostearate | 1.5 – 3.5 |
| cetyl alcohol | 1.25 – 2.5 |
| 2-ethylhexyl palmitate | 8.00 – 14.00 |
| isostearic acid | 0.5 – 4.00 |
| polyoxyethylene stearate | 0.2 – 1.50 |
| sorbitan tristearate | 0.1 – 0.4; |

(B) a water phase consisting essentially of, in parts by weight,

| | |
|---|---|
| synthetic hectorite clay | 1.80 – 3.96 |
| sodium acid pyrophosphate | |
| propylene glycol | 0.30 |
| a preservative | effective amount |
| triethanolamine | 1.00 |
| milk protein | 1.25 |
| water | balance to make 100; and |

(C) about 0.1 part of an encapsulated active base which consists essentially of, in percent by weight,

| | |
|---|---|
| hydroxyethyl cellulose | 0.5 – 2.5 |
| synthetic hectorite clay | 0.45 – 1.8 |
| sodium acid pyrophosphate | 0.05 – 2.00 |
| coloring | 5 –10 |
| casein | 0.5 – 3.00 |
| a preservative | effective amount |
| water | balance |

* * * * *

UNITED STATES PATENT OFFICE
CERTIFICATE OF CORRECTION

Patent No. 4,087,555                    Dated   May 2, 1978

Inventor(s)   Gabriel Barnett, et al

It is certified that error appears in the above-identified patent and that said Letters Patent are hereby corrected as shown below:

Column 4, line 67: After "scope" insert --to--.

Column 7, lines 7 and 8: "rective" should be --reactive--.

Signed and Sealed this

Twenty-eighth Day of November 1978

[SEAL]

Attest:

RUTH C. MASON
Attesting Officer

DONALD W. BANNER
Commissioner of Patents and Trademarks